(12) United States Patent
Okumura et al.

(10) Patent No.: US 9,314,454 B2
(45) Date of Patent: Apr. 19, 2016

(54) ORAL CAVITY DISINTEGRATING TABLET AND METHOD OF PRODUCING THE SAME

(75) Inventors: Tomonori Okumura, Osaka (JP);
Nobuko Hamaguchi, Osaka (JP);
Yasufumi Okamura, Osaka (JP)

(73) Assignee: Sawai Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/810,779

(22) PCT Filed: Dec. 26, 2008

(86) PCT No.: PCT/JP2008/073842
§ 371 (c)(1),
(2), (4) Date: Jun. 25, 2010

(87) PCT Pub. No.: WO2009/084678
PCT Pub. Date: Jul. 9, 2009

(65) Prior Publication Data
US 2010/0278930 A1    Nov. 4, 2010

(30) Foreign Application Priority Data
Dec. 28, 2007 (JP) ................................ 2007-340704

(51) Int. Cl.
| | | |
|---|---|---|
| A61K 9/14 | (2006.01) | |
| A61K 31/4422 | (2006.01) | |
| A61K 9/00 | (2006.01) | |
| A61K 9/20 | (2006.01) | |

(52) U.S. Cl.
CPC ........... *A61K 31/4422* (2013.01); *A61K 9/0056* (2013.01); *A61K 9/2018* (2013.01); *A61K 9/2054* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 5,576,014 A | * | 11/1996 | Mizumoto et al. |
| 6,455,053 B1 | * | 9/2002 | Okada et al. |
| 2001/0010825 A1 | | 8/2001 | Shimizu et al. |
| 2001/0014340 A1 | * | 8/2001 | Ohta et al. |
| 2003/0215500 A1 | | 11/2003 | Ohta et al. |
| 2004/0047904 A1 | | 3/2004 | Ohta et al. |
| 2005/0152973 A1 | | 7/2005 | Murakami et al. |
| 2005/0208127 A1 | | 9/2005 | Ogasawara et al. |
| 2006/0159759 A1 | * | 7/2006 | Ohta et al. ................ 424/472 |

FOREIGN PATENT DOCUMENTS

| | | |
|---|---|---|
| EP | 0 745 382 A1 | 12/1996 |
| EP | 0 914 818 A1 | 5/1999 |
| EP | 1 153 616 A1 | 11/2001 |
| EP | 1 203 580 A1 | 5/2002 |
| EP | 1 488 811 A1 | 12/2004 |
| EP | 1 552 851 A1 | 7/2005 |
| EP | 1 695 699 A1 | 8/2006 |
| EP | 1 897 558 A1 | 3/2008 |
| EP | 1 961 413 A1 | 8/2008 |
| JP | 11-310539 A | 11/1999 |
| JP | 2000-103731 A | 4/2000 |
| JP | 2001-58944 A | 3/2001 |
| WO | WO 95/20380 A1 | 8/1995 |
| WO | WO 97/47287 A1 | 12/1997 |
| WO | WO 99/36097 A1 | 7/1999 |
| WO | WO 99/43306 A1 | 9/1999 |
| WO | WO 00/06126 A1 | 2/2000 |
| WO | WO 00/47233 A1 | 8/2000 |
| WO | WO 01/76565 A1 | 10/2001 |
| WO | WO 03/041698 A1 | 5/2003 |
| WO | WO 03/103713 A1 | 12/2003 |
| WO | WO 2006/132440 A1 | 12/2006 |

OTHER PUBLICATIONS

"Handbook of Pharmaceutical Excipients," 5/e, Rowe, R., et al., eds. (2006).*
European Patent Office, Extended European Search Report in European Patent Application No. 08868222.4 (Apr. 1, 2011).

* cited by examiner

*Primary Examiner* — David J Blanchard
*Assistant Examiner* — Daniel F Coughlin
(74) *Attorney, Agent, or Firm* — Leydig, Voit & Mayer, Ltd.

(57) ABSTRACT

The invention provides an orally disintegrating tablet containing (a) one or more saccharides or sugar alcohols selected from the group consisting of mannitol, lactose, xylitol, sucrose, erythritol and glucose and (b) low substituted hydroxypropylcellulose and substantially free of a starch disintegrant, which tablet is produced by steps of granulating a composition containing the above-mentioned components (a) and (b) by an agitation granulation method, and compression-molding the obtained granulation product. The invention also provides a method of producing an orally disintegrating tablet substantially free of a starch disintegrant, including steps of granulating a composition containing the above-mentioned components by an agitation granulation method, and compression-molding the obtained granulation product.

6 Claims, No Drawings

ORAL CAVITY DISINTEGRATING TABLET AND METHOD OF PRODUCING THE SAME

TECHNICAL FIELD

The present invention relates to an orally disintegrating tablet which is rapidly disintegrated in an oral cavity, is easy to produce, has desired appropriate hardness, and is superior in the storage stability, and production method thereof.

BACKGROUND ART

With the advent of the aging society and for improved compliance of patients, the significance of orally disintegrating tablets which can be taken without water has been emphasized in recent years. As conventional orally disintegrating tablets, those produced by lyophilizing with substances such as gelatin and the like in a container, those obtained by wet-tableting wet powder or granulated particles, and the like are known. However, such tablets are sometimes cracked or chipped during transport, do not entirely have sufficient hardness, and also require complicated production methods.

Furthermore, even if conventional orally disintegrating tablets have good tablet hardness immediately after production, their hardness will be likely to decrease during storage because of moisture absorption, so they will be cracked or chipped when pushing out of PTP sheet. Various attempts have been made to solve these defects and, for example, the following techniques have been proposed in the documents.

Patent document 1 discloses that an orally disintegrating compressed molding shows quick disintegration and dissolution in the oral cavity, which comprises a difficultly moldable saccharide and a readily moldable saccharide. However, production of the orally disintegrating tablet described in the document essentially requires humidification and drying steps after tableting at low pressure, which necessitates a large number of production steps and cumbersome operations. Moreover, even though a certain level of hardness is achieved immediately after production, the problem of decreased hardness due to moisture absorption during storage remains unsolved.

Patent document 2 discloses that a tablet comprising a sugar alcohol or a saccharide with an average particle diameter of not more than 30 μm, an active ingredient, and a disintegrant, has shown good tablet hardness immediately after production. However, it does not describe whether the hardness can also be maintained during storage.

Patent document 3 discloses an orally disintegrating, molded composition which easily disintegrates in an oral cavity, containing organic acid(s), carbonate(s), network maintaining agent(s), and color-change preventing agent(s), wherein a network is formed among said organic acid(s) said carbonate(s), said network maintaining agent(s) and said color-change preventing agent(s), wherein said network maintaining agent is at least one water insoluble solid material selected from a group composed of corn starch, potato starch, sodium carboxymethyl starch, crystalline cellulose, low substituted hydroxypropylcellulose, and croscarmellose sodium, wherein said color-change preventing agent is at least one water soluble sugar selected from a group composed of erythritol, xylitol, mannitol, and lactose, and herein 25.0-625.0 weight part of said network maintaining agent and 25.0-937.5 weight part of said color-change preventing agent are formulated for 100 weight part of a mixture of said organic acid and said carbonate. However, since the tablets require removal of carbon dioxide gas and water therefrom by heating the tablet after tableting, special production facility and technique are necessary, and the operation is also cumbersome. Moreover, it is impossible to apply the technique of this document to active ingredients unstable to temperature and water.

Patent document 4 discloses a rapidly disintegrable solid preparation which comprises 1) a pharmacologically active ingredient, 2) a sugar and 3) a low substituted hydroxypropylcellulose having 5 wt % or more to less than 7 wt % of hydroxypropoxyl group. However, since the low substituted hydroxypropylcellulose used in the document is not commercially available, it is not entirely widely available.

Patent document 5 discloses a tablet which comprises a starch, a water-soluble excipient and a medicament and substantially not containing a binder other than starch, patent document 6 discloses a quickly disintegrating solid preparation comprising a) an active ingredient, b) a saccharide or sugar alcohol with the average particle diameter of 30 μm to 300 μm, c) a disintegrating agent, and d) a cellulose compound, and patent document 7 discloses an orally disintegrating composition, which is a molded composition rapidly disintegrated in an oral cavity, and comprising a filler comprised of sugar alcohol, a disintegrating agent and a lubricant, wherein the penetration rate of ethanol into this lubricant is $3.0 \times 10^{-3}$ g$^2$/sec or above. In any documents, the hardness is not sufficient for practical use since the tablet with the tablet hardness described therein may be cracked or chipped. In addition, the documents do not describe hardness and stability of the tablets during storage.

Patent document 8 discloses an intraorally rapidly disintegrating tablet, which comprises D-mannitol having an average particle diameter of 31 μm to 80 μm, an active ingredient, a disintegrant, and stearic acid or a metallic stearate in an amount of 0.01 wt % to 0.5 wt %. However, a special facility of an external lubrication system is essential.

Therefore, in the prior art, an orally disintegrating tablet having practically sufficient tablet hardness and storage stability, which can be produced using usually available pharmaceutical manufacturing apparatuses and machines and according to convenient method, is not known.

patent document 1: WO 95/20380
patent document 2: WO 97/47287
patent document 3: JP-A-11-310539
patent document 4: JP-A-2000-103731
patent document 5: WO 00/47233
patent document 6: JP-A-2001-58944
patent document 7: WO 2001/076565
patent document 8: WO 2003/103713

DISCLOSURE OF THE INVENTION

Problems to be Solved by the Invention

The present invention provides an orally disintegrating tablet which is rapidly disintegrated in an oral cavity, is easy to produce, has desired appropriate hardness, and is superior in the storage stability, and production method thereof.

Means of Solving the Problems

The present inventors have conducted intensive studies and found that an orally disintegrating tablet, which is rapidly disintegrated in an oral cavity and has desired appropriate hardness, can be easily produced by simple steps including adding, to an orally disintegrating tablet comprises, (a) one or more saccharides or sugar alcohols selected from the group consisting of mannitol, lactose, xylitol, sucrose, erythritol and glucose and (b) low substituted hydroxypropylcellulose, and, the tablet is produced by, steps of granulating a composition containing the above-mentioned components (a) and (b) by an agitation granulation method, and compression-molding the obtained granulation product. In addition, the present inventors have also found that the storage stability can be improved by substantially not using a starch disintegrant in the above-mentioned method. Based on these findings, they have further studied and completed the present invention.

The present invention relates to the following [1]-[10].

[1] An orally disintegrating tablet comprising (a) one or more saccharides or sugar alcohols selected from the group consisting of mannitol, lactose, xylitol, sucrose, erythritol and glucose and (b) low substituted hydroxypropylcellulose and substantially free of a starch disintegrant, which tablet is produced by steps of granulating a composition comprising the above-mentioned components (a) and (b) by an agitation granulation method, and compression-molding the obtained granulation product.

[2] The orally disintegrating tablet of the above-mentioned [1], comprising the aforementioned component (a), the aforementioned component (b), and (c) one or more saccharides or sugar alcohols selected from the group consisting of powder hydrogenated maltose starch syrup, maltose, maltitol, sorbitol and trehalose, which tablet is produced by steps of granulating a composition comprising the above-mentioned components (a), (b) and (c) by an agitation granulation method, and compression-molding the obtained granulation product.

That is, an orally disintegrating tablet comprising (a) one or more saccharides or sugar alcohols selected from the group consisting of mannitol, lactose, xylitol, sucrose, erythritol and glucose, (b) low substituted hydroxypropylcellulose and (c) one or more saccharides or sugar alcohols selected from the group consisting of powder hydrogenated maltose starch syrup, maltose, maltitol, sorbitol and trehalose, and substantially free of a starch disintegrant, which tablet is produced by steps of granulating a composition comprising the above-mentioned components (a), (b) and (c) by an agitation granulation method, and compression-molding the obtained granulation product.

[3] The orally disintegrating tablet of the above-mentioned [1] or [2], wherein the saccharide or sugar alcohol of the aforementioned component (a) has an average particle size of not more than 50 μm.

[4] The orally disintegrating tablet of any one of the above-mentioned [1] to [3], wherein the saccharide or sugar alcohol of the aforementioned component (a) is mannitol or lactose.

[5] The orally disintegrating tablet of any one of the above-mentioned [2] to [4], wherein the saccharide or sugar alcohol of the aforementioned component (c) is powder hydrogenated maltose starch syrup or maltose.

[6] A method of producing an orally disintegrating tablet substantially free of a starch disintegrant, comprising steps of granulating a composition comprising (a) one or more saccharides or sugar alcohols selected from the group consisting of mannitol, lactose, xylitol, sucrose, erythritol and glucose and (b) low substituted hydroxypropylcellulose by an agitation granulation method, and compression-molding the obtained granulation product.

[7] The production method of the above-mentioned [6], comprising steps of granulating a composition comprising the aforementioned component (a), the aforementioned component (b), and (c) one or more saccharides or sugar alcohols selected from the group consisting of powder hydrogenated maltose starch syrup, maltose, maltitol, sorbitol and trehalose by an agitation granulation method and compression-molding the obtained granulation product.

That is, a method of producing an orally disintegrating tablet substantially free of a starch disintegrant, comprising steps of granulating a composition comprising (a) one or more saccharides or sugar alcohols selected from the group consisting of mannitol, lactose, xylitol, sucrose, erythritol and glucose, (b) low substituted hydroxypropylcellulose, and (c) one or more saccharides or sugar alcohols selected from the group consisting of powder hydrogenated maltose starch syrup, maltose, maltitol, sorbitol and trehalose by an agitation granulation method, and compression-molding the obtained granulation product.

[8] The production method of the above-mentioned [6] or [7], wherein the saccharide or sugar alcohol of the aforementioned component (a) has an average particle size of not more than 50 μm.

[9] The production method of any one of the above-mentioned [6] to [8], wherein the saccharide or sugar alcohol of the aforementioned component (a) is mannitol or lactose.

[10] The production method of any one of the above-mentioned [7]-[9], wherein the saccharide or sugar alcohol of the aforementioned component (c) is powder hydrogenated maltose starch syrup or maltose.

Effect of the Invention

The orally disintegrating tablet of the present invention can be easily produced by simple steps, is rapidly disintegrated in an oral cavity, has desired appropriate hardness, and is superior in the storage stability since it shows only a small decrease in the hardness and a small increase in the tablet thickness even under high temperature and/or high humidity conditions without any packages.

Using the production method of the present invention, an orally disintegrating tablet, which is rapidly disintegrated in an oral cavity, has desired appropriate hardness, and is superior in the storage stability since it shows only a small decrease in the hardness and a small increase in the tablet thickness even under high temperature and/or high humidity conditions without any packages, can be easily produced by simple steps. In addition, using the production method of the present invention, tableting troubles during tableting, such as capping and binding to a die inner wall and the like can be suppressed.

BEST MODE FOR CARRYING OUT THE INVENTION

The present invention is explained in detail in the following.

In the present specification, an orally disintegrating tablet means a tablet that is rapidly disintegrated by saliva in an oral cavity.

The orally disintegrating tablet of the present invention comprises (a) one or more saccharides or sugar alcohols selected from the group consisting of mannitol (particularly, D-mannitol), lactose (particularly, lactose hydrate), xylitol, sucrose, erythritol and glucose (to be also referred to as component (a) in the present specification) and (b) low substituted hydroxypropylcellulose (to be also referred to as component (b) in the present specification).

As component (a), mannitol and lactose are preferable.

The content of component (a) is preferably 50-95 wt %, more preferably 70-90 wt %, of the weight of the preparation. Component (a) can also be optionally dissolved in water and the like as mentioned below and used as a binding solution for agitation granulation. The content of the above-mentioned component (a) also includes the amount used as the binding solution. When used as the binding solution, the amount thereof is preferably less than 10 wt %, more preferably about 2-5 wt %, of the content of the above-mentioned component (a).

The average particle size of the saccharides and sugar alcohols of component (a) is preferably not more than 50 μm, more preferably 10-20 μm. When the average particle size exceeds 50 μm, the disintegration time tends to be extended.

The average particle size of the saccharides and sugar alcohols of the above-mentioned component (a) means their initial average particle size of the starting materials before being subjected to the agitation granulation and means that they have a particle size within the above-mentioned range, and the average particle size may change during the subsequent production processes and storage of the preparation.

The saccharides and sugar alcohols of component (a) having an average particle size within the above-mentioned range are commercially available. Alternatively, the commercially available products may be pulverized with a conventional method to adjust the particle size and thereafter used.

Here, the average particle size in the present specification shows a 50% accumulated particle size in the particle size distribution measured based on a dry method using an airflow-type disperser.

In the present invention, the low substituted hydroxypropylcellulose does not require a particular limitation on the grade and the like, and a commercially available product can be used. For example, low substituted hydroxypropylcellulose having a hydroxypropoxyl group content of about 7.0-12.9 wt % can be used.

The content of the low substituted hydroxypropylcellulose is preferably 3-20 wt %, more preferably 5-15 wt %, of the weight of the preparation.

The orally disintegrating tablet of the present invention preferably contains (c) one or more saccharides or sugar alcohols selected from the group consisting of powder hydrogenated maltose starch syrup, maltose, maltitol, sorbitol and trehalose (to be also referred to as component (c) in the present specification). The presence of component (c) further increases the tablet hardness.

As component (c), powder hydrogenated maltose starch syrup and maltose are preferable.

The content of component (c) is preferably 0.1-5 wt %, more preferably 0.1-1 wt %, of the weight of the preparation.

The orally disintegrating tablet of the present invention does not substantially contain a starch disintegrant (e.g., corn starch, sodium carboxymethyl starch, rice starch, wheat starch, pregelatinized starch, partly pregelatinized starch etc.).

Here, "substantially free of" in the present specification means absence of an amount that adversely influences the storage stability of preparations. Specifically, the content of the starch disintegrant is preferably not more than 5 wt %, more preferably not more than 3 wt %, still more preferably not more than 1 wt %, of the weight of the preparation.

The orally disintegrating tablet of the present invention preferably contains thaumatin. The content of thaumatin is preferably 0.1-5 wt %, more preferably 0.1-1 wt %, of the weight of the preparation. Thaumatin is a sweetener generally added for masking the bitterness of an active ingredient. In the present invention, the presence of thaumatin provides effects of improved moldability during production and increased hardness.

Besides the above-mentioned components, the orally disintegrating tablet of the present invention may contain additives generally used for solid preparations. The additive is, for example, excipient, disintegrant other than starch disintegrant, binder, lubricant, fluidizer, corrigent, sweetening agent, coating agent, colorant, flavor and the like. The content of these additives is not particularly limited and may be appropriately selected from an amount conventionally used in the pharmaceutical field. The total amount of the additives except for components (a) and (b) (when component (c) is contained, the total amount of the additives except for components (a)-(c)) is preferably not more than 50 wt %, more preferably not more than 25 wt %, of the weight of the preparation.

The orally disintegrating tablet of the present invention may contain an active ingredient such as a pharmaceutical component and the like, or may be used as a placebo without an active ingredient. While the active ingredient is not particularly limited, for example, (±)-3-ethyl 5-methyl 2-[(2-aminoethoxy)methyl]-4-(o-chlorophenyl)-1,4-dihydro-6-methyl-3,5-pyridinedicarboxylate benzenesulfonate, famotidine, atorvastatin calcium hydrate, zolpidem tartrate, sumatriptan succinate, simvastatin, pravastatin sodium, glimepiride, taltirelin hydrate and the like can be mentioned. The content of the active ingredient may be appropriately determined based on the amount used for clinical application, and it is preferably not more than 50 wt %, more preferably not more than 25 wt %, of the weight of the preparation.

The orally disintegrating tablet of the present invention is characterized by production including steps of granulating a composition containing the above-mentioned components (a) and (b) (preferably the above-mentioned components (a), (b) and (c)) by an agitation granulation method, and compression-molding the obtained granulation product. It is considered that since the granulation product becomes spherical by agitation granulation, tableting troubles (particularly, binding to die inner wall) in the subsequent compression-molding step are prevented in the present invention.

The production method of the orally disintegrating tablet of the present invention is explained in detail in the following.

1. Granulation Step

The above-mentioned components (a) and (b) (preferably the above-mentioned components (a), (b) and (c)), an optional active ingredient and/or an optional additive are mixed. The additive is, for example, excipients (e.g., talc), disintegrants other than starch disintegrants (e.g., crospovidone), sweetening agents, colorants, flavors and the like. The active ingredient may be mixed with an excipient (e.g., talc) first and then coated with a coating agent (e.g., aqueous ethylcellulose dispersion, triacetine) for the purpose of masking bitterness and the like.

The above-mentioned mixture is granulated by an agitation granulation method. The agitation granulation method is also generally referred to as a high-speed agitation granulation method. Here, the (high-speed) agitation granulation method is a method including adding dropwise or spraying a binder solution on a mixed powder by rotating the main wings set on the bottom of a granulating machine to form large particles, and grinding the particles by a chopper on the side wall to give granules desired particle size (Yoshihisa SAGAWA, "Pharmaceutical Product Preparation Technique", CMC Publishing CO., LTD., published in 2002, page 108).

The granulation by an agitation granulation method can be performed by using what is called an agitation granulator (also referred to as a high-speed agitation granulator) (e.g., high-speed mixer, LFS-GS-2J (manufactured by Fukae Powtec); VERTICAL GRANULATOR (manufactured by POWREX CORPORATION); NEW SPEED KNEADER (manufactured by OKADA SEIKO CO., LTD.) etc.). The rotation speed of the main wings and chopper is not particularly limited, and may be appropriately selected from the range generally used at agitation granulation. Specifically, a binding solution (e.g., water or, where necessary, other additives may be blended) is added to the above-mentioned mixture in the agitation granulator, and the mixture is granulated. When thaumatin is added in the present invention, though not particularly limited, it may be added to the binding solution.

2. Compression Molding Step

To the granulation product obtained in the granulation step is added an optional active ingredient and/or an optional additive (e.g., fluidizers (e.g., light anhydrous silicic acid), lubricants (e.g., magnesium stearate, sodium stearyl fumarate, calcium stearate), flavors), and the mixture is blended and compression-molded by a tableting machine and the like. The compression molding pressure (tableting pressure) may be appropriately selected from the range generally used at tablet production. While the pressure is not particularly limited, it is preferably not less than 200 kg.

The orally disintegrating tablet of the present invention produced as mentioned above has desired appropriate hardness, is rapidly disintegrated in an oral cavity, and shows superior storage stability, even though it can be easily produced without cumbersome steps of humidification and drying after tableting and a special facility of an external lubrication system.

The hardness of the orally disintegrating tablet of the present invention is generally about 3-6 kg when the tablet has a diameter of 6-7 mm and a thickness of about 3 mm. Here, the hardness of the tablet in the present specification is a value measured by a Schleuniger tablet hardness tester (Dr. Schleuniger Pharmatron AG).

While the disintegration time of the orally disintegrating tablet of the present invention in an oral cavity varies depending on the form of preparation, dose and the like, it is generally within 60 sec, preferably within 30 sec.

The orally disintegrating tablet of the present invention is not particularly limited as regards the size and form, and may be a scored tablet having a cleavage line.

The orally disintegrating tablet of the present invention can be ingested without water.

EXAMPLES

The present invention is explained in more detail in the following by referring to Examples, Comparative Examples and Experimental Examples, which are not to be construed as limitative.

Example 1

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 20.79 g) (15.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (280.41 g, average particle size 10-20 μm), low substituted hydroxypropylcellulose (39.6 g, Shin-Etsu Chemical Co., Ltd.), powder hydrogenated maltose starch syrup (1.2 g), aspartame (7.2 g) and a colorant (trace amount) were mixed in the agitation granulator (LFS-GS-2J, Fukae Powtec). To the obtained mixture was added purified water (120 g), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (7.2 g) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of 470-510 kg to give an orally disintegrating tablet (120.0 mg) containing 5.0 mg (based on the base) of the active ingredient per tablet.

The hardness of the obtained orally disintegrating tablet was about 4 kg, and the oral disintegration time was about 20-30 sec.

In Example 1, capping and binding to a die inner wall did not occur during tableting, and cracks, chips and scratches were not confirmed on the obtained tablets.

Therefrom it was confirmed that tableting troubles can be prevented by the production method of the present invention, even when corn starch having a function as a binder was not added and only purified water was used.

In addition, using the production method of the present invention, an orally disintegrating tablet having good tablet hardness could be easily produced even without cumbersome steps of humidification and drying after tableting and a special facility of an external lubrication system.

Example 2

Famotidine (30.0 g) and talc (trace amount) were mixed in the fluid bed granulator (MP-01/SFP, POWREX CORPORATION), and then they were successively coated with a coating solution which was separately prepared by mixing an aqueous dispersion of ethylcellulose (30 g (solid content 9.0 g)) and triacetine (2.25 g). To the obtained coated granules were added D-mannitol (239.55 g, average particle size 10-20 μm), low substituted hydroxypropylcellulose (60.0 g, Shin-Etsu Chemical Co., Ltd.), powder hydrogenated maltose starch syrup (1.2 g) and aspartame (7.2 g) and they were mixed in the agitation granulator (LFS-GS-2J, Fukae Powtec). To the obtained mixture was added purified water (120 g), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (7.2 g) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of about 670 kg to give an orally disintegrating tablet (120.0 mg) containing 10.0 mg of famotidine per tablets.

The hardness of the obtained orally disintegrating tablet was about 3.5 kg, and the oral disintegration time was about 20-30 sec.

In Example 2, capping and binding to a die inner wall did not occur during tableting, and cracks, chips and scratches were not confirmed on the obtained tablets.

Example 3

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 13.88 g) (10.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (269.72 g, average particle size 10-20 μm), low substituted hydroxypropylcellulose (38.0 g, Shin-Etsu Chemical Co., Ltd.), powder hydrogenated maltose starch syrup (1.2 g), aspartame (6.8 g) and a colorant (trace amount) were mixed in the agitation granulator (LFS-GS-2J, Fukae Powtec). To the obtained mixture was added purified water (112 g), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (6.8 g) were added and mixed therewith (total solid content 340.0 g). The obtained mixture was tableted by the single punch tableting machine (KIKUSUI SEISAKUSHO LTD.) with a φ6R surface punch at a tableting pressure of about 600 kg to give an orally disintegrating tablet (85.0 mg) containing 2.5 mg (based on the base) of the active ingredient per tablet.

The tablet thickness of the obtained orally disintegrating tablet was 2.80 mm, the hardness was about 4.5 kg, and the oral disintegration time was about 20-30 sec.

In Example 3, capping and binding to a die inner wall did not occur during tableting, and cracks, chips and scratches were not confirmed on the obtained tablets.

Example 4

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 13.88 g) (10.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (269.32 g, average particle size 10-20 μm), low substituted hydroxypropylcellulose (38.0 g, Shin-Etsu Chemical Co., Ltd.), powder hydrogenated maltose starch syrup (1.2 g), aspartame (6.8 g) and a colorant (trace amount) were mixed in the agitation granulator (LFS-GS-2J, Fukae Powtec). To the obtained mixture was added thaumatin (0.4 g) dissolved in purified water (112 g), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (6.8 g) were added and mixed therewith (total solid content 340.0 g). The obtained mixture was tableted by the single punch tableting machine (KIKUSUI SEISAKUSHO LTD.) with a φ6R surface punch at a tableting pressure of about 600 kg to give an orally disintegrating tablet (85.0 mg) containing 2.5 mg (based on the base) of the active ingredient per tablets.

The tablet thickness of the obtained orally disintegrating tablet was 2.74 mm, the hardness was about 5.5 kg, and the oral disintegration time was about 20-30 sec.

In Example 4, capping and binding to a die inner wall did not occur during tableting, and cracks, chips and scratches were not confirmed on the obtained tablets.

Example 5

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 20.79 g) (15.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (281.11 g, average particle size 10-20 μm), low substituted hydroxypropylcellulose (39.6 g, Shin-Etsu Chemical Co., Ltd.), powder hydrogenated maltose starch syrup (1.2 g), aspartame (3.6 g) and a colorant (trace amount) were mixed in the agitation granulator (LFS-GS-2J, Fukae Powtec). To the obtained mixture was added thaumatin (0.9 g) dissolved in purified water (120 g), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (7.2 g) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of 510-570 kg to give an orally disintegrating tablet (120.0 mg) containing 5.0 mg (based on the base) of the active ingredient per tablet.

The tablet thickness of the obtained orally disintegrating tablet was 2.98 mm, the hardness was about 4.8 kg, and the oral disintegration time was about 20-30 sec.

In Example 5, capping and binding to a die inner wall did not occur during tableting, and cracks, chips and scratches were not confirmed on the obtained tablets.

Example 6

In the same manner as in Example 5 except that lactose hydrate (281.11 g, average particle size about 30 μm) was used instead of D-mannitol (281.11 g), and the tableting pressure was changed to 520-570 kg, an orally disintegrating tablet was produced.

The tablet thickness of the obtained orally disintegrating tablet was 2.95 mm, the hardness was about 4.0 kg, and the oral disintegration time was about 20-30 sec.

In Example 6, capping and binding to a die inner wall did not occur during tableting, and cracks, chips and scratches were not confirmed on the obtained tablets.

The preparation of Example 5 produced using D-mannitol as a base formulation and the preparation of Example 6 produced using lactose as a base formulation each had an appropriate hardness, were rapidly disintegrated in an oral cavity, and had a function as an orally disintegrating tablet. Therefore, in the present invention, both saccharide and sugar alcohol can be used as a base for formulation.

Example 7

In the same manner as in Example 5 except that maltose (1.2 g) was used instead of powder hydrogenated maltose starch syrup (1.2 g), and the tableting pressure was changed to 520-570 kg, an orally disintegrating tablet was produced.

The tablet thickness of the obtained orally disintegrating tablet was 2.98 mm, the hardness was about 5.0 kg, and the oral disintegration time was about 20-30 sec.

In the preparation of Example 7 produced by adding maltose instead of the powder hydrogenated maltose starch syrup of Example 5, tableting troubles such as capping and binding to a die inner wall and the like were not found as in Example 5, and similar results of hardness and oral disintegration time to Example 5 were obtained. Hence, similar effects can be obtained by adding a saccharide having high moldability, which is not limited to powder hydrogenated maltose starch syrup.

Example 8

In the same manner as in Example 5 except that the tableting pressure was changed to 470-510 kg, an orally disintegrating tablet was produced.

The tablet thickness of the obtained orally disintegrating tablet was 3.00 mm, the hardness was about 4 kg, and the oral disintegration time was about 20 sec.

Example 9

In the same manner as in Example 5 except that the active ingredient and powder hydrogenated maltose starch syrup were not used, D-mannitol (281.11 g) was changed to D-mannitol (305.1 g, average particle size 10-20 μm), and the tableting pressure was changed to 500-550 kg, an orally disintegrating tablet was produced.

The tablet thickness of the obtained orally disintegrating tablet was 3.05 mm, the hardness was about 3.5 kg, and the oral disintegration time was about 20 sec.

In Examples 8 and 9, capping and binding to a die inner wall did not occur during tableting, and cracks, chips and scratches were not confirmed on the obtained tablets.

In addition, from the results of Examples 8 and 9, it was shown that an orally disintegrating tablet having a sufficient hardness and showing a suitable oral disintegration time can be obtained by the formulation and production method of the present invention using a D-mannitol-low substituted hydroxypropylcellulose formulation system and agitation granulation, even without addition of powder hydrogenated maltose starch syrup.

Comparative Example 1

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 20.79 g) (15.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (250.41 g, average particle size 10-20 μm), corn starch (30.0 g), low substituted hydroxypropylcellulose (10.8 g, Shin-Etsu Chemical Co., Ltd.), aspartame (3.0 g), light anhydrous silicic acid (1.8 g) and a colorant (trace amount) were mixed in the fluid bed granulator (MP-01, POWREX CORPORATION). To the obtained mixture was added 10% aqueous D-mannitol solution (360 g (solid content 36.0 g)) by spraying, and the mixture was successively granulated in the fluid bed granulator (MP-01, POWREX CORPORATION) and dried. The granulation product was sieved through a sieve No. 22. The sieved product was placed in a bag, and a flavor (trace amount) and magnesium stearate (7.2 g (theoretical amount)) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of 500-600 kg to give an orally disintegrating tablet (120.0 mg) containing 5.0 mg (based on the base) of the active ingredient per tablet.

In Comparative Example 1, capping occurred during tableting, and the tablet was cracked. In addition, binding to a die inner wall occurred, and scratches were confirmed on the side face (band) of the tablets.

Comparative Example 2

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 20.79 g) (15.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (249.21 g, average particle size 10-20 μm), corn starch (30.0 g), low substituted hydroxypropylcellulose (10.8 g, Shin-Etsu Chemical Co., Ltd.), powder hydrogenated maltose starch syrup (1.2 g), aspartame (3.0 g), light anhydrous silicic acid (1.8 g) and a colorant (trace amount) were mixed in the fluid bed granulator (MP-01, POWREX CORPORATION). To the obtained mixture was added 10% aqueous D-mannitol solution (360 g (solid content 36.0 g)) by spraying, and the mixture was successively granulated in the fluid bed granulator (MP-01, POWREX CORPORATION) and dried. The granulation product was sieved through a sieve No. 22. The sieved product was placed in a bag, and a flavor (trace amount) and magnesium stearate (7.2 g) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of 570-660 kg to give an orally disintegrating tablet (120.0 mg) containing 5.0 mg (based on the base) of the active ingredient per tablet.

The hardness of the obtained orally disintegrating tablet was about 5 kg, and the oral disintegration time was about 30 sec.

In Comparative Example 2, binding to a die inner wall occurred during tableting, and scratches were confirmed on the side face (band) of the tablets.

Comparative Example 3

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 6.93 g) (5.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (91.47 g), corn starch (10.0 g), low substituted hydroxypropylcellulose (3.6 g, Shin-Etsu Chemical Co., Ltd.), powder hydrogenated maltose starch syrup (0.4 g), aspartame (1.0 g) and a colorant (trace amount) were mixed in a mortar. To the obtained mixture was added 10% aqueous D-mannitol solution (30 g (solid content 3.0 g)), and the mixture was successively granulated in the mortar. The granulation product was dried in the aeration type dryer (Toyama Sangyo Co., Ltd.) at 60° C., and sieved through a sieve No. 22. The sieved product was placed in a bag, and light anhydrous silicic acid (1.2 g), a flavor (trace amount) and magnesium stearate (2.4 g) were added and mixed therewith (total solid content 120.0 g). The obtained mixture was tableted by the single punch tableting machine (KIKUSUI SEISAKUSHO LTD.) with a φ7R surface (with a cleavage line) punch at a tableting pressure of 550-650 kg to give an orally disintegrating tablet (120.0 mg) containing 5.0 mg (based on the base) of the active ingredient per tablet.

The hardness of the obtained orally disintegrating tablet was about 5 kg, and the oral disintegration time was about 30 sec.

In Comparative Example 3, granulation was performed according to a kneading method. Binding to a die inner wall occurred during tableting, and scratches were confirmed on the side face (band) of the tablets.

Comparative Example 4

(±)-3-Ethyl 5-methyl 2-[(2-aminoethoxy)methyl]-4-(o-chlorophenyl)-1,4-dihydro-6-methyl-3,5-pyridinedicarboxylate benzenesulfonate (active ingredient, 20.79 g) (15.0 g as (±)-3-ethyl 5-methyl 2-[(2-aminoethoxy)methyl]-4-(o-chlorophenyl)-1,4-dihydro-6-methyl-3,5-pyridinedicarboxylate), D-mannitol (270.21 g, average particle size 10-20 μm), corn starch (30.0 g), low substituted hydroxypropylcellulose (10.8 g, Shin-Etsu Chemical Co., Ltd.), powder hydrogenated maltose starch syrup (1.2 g), aspartame (7.2 g) and a colorant (trace amount) were mixed in the agitation granulator (LFS-GS-2J, Fukae Powtec). To the obtained mixture was added 10% aqueous D-mannitol solution (90 g (solid content 9.0 g)), and the mixture was successively granulated in the agitation granulator (LFS-GS-2J, Fukae Powtec). The granulation product was dried in the aeration type dryer (Toyama Sangyo Co., Ltd.) at 60° C., and sieved through a sieve No. 22. The sieved product was placed in a bag, and light anhydrous silicic acid (3.6 g), a flavor (trace amount) and sodium stearyl fumarate (7.2 g) were added and mixed therewith (total solid content 360.0 g). The obtained mixture was tableted by the single punch tableting machine (KIKUSUI SEISAKUSHO LTD.) with a φ7R surface (with a cleavage line) punch at a tableting pressure of about 470-550 kg to give an orally disintegrating tablet (120.0 mg) containing 5.0 mg (based on the base) of the active ingredient per tablet.

The hardness of the obtained orally disintegrating tablet immediately after the production was about 4 kg, and the oral disintegration time was about 20-30 sec.

Experimental Example 1

To examine the storage stability of the orally disintegrating tablet of Example 1, the orally disintegrating tablets of Example 1 and Comparative Example 4 were respectively stored without any packages under conditions of 25° C., 75% RH and 40° C., 75% RH each for one month, and the hardness (kg) was measured. The results are shown in Table 1.

TABLE 1

| storage conditions | Example 1 | Comparative Example 4 |
|---|---|---|
| At time of start of test | 4.0 kg | 4.2 kg |
| (without packaging) 25° C., 75% RH, one month | 3.5 kg | 2.8 kg |
| (without packaging) 40° C., 75% RH, one month | 3.7 kg | 2.3 kg |

Table 1 shows that in Example 1, the decrease of hardness after one month storage without any packages under the conditions of 25° C., 75% RH and 40° C., 75% RH was 0.5 kg and 0.3 kg, respectively. On the contrary, it was 1.4 kg and 1.9 kg in Comparative Example 4, respectively.

From the above-mentioned results, the orally disintegrating tablet of Comparative Example 4 containing corn starch showed a large decrease in the hardness even though it was produced by agitation granulation. On the other hand, the orally disintegrating tablet of Example 1, which did not contain a starch disintegrant such as corn starch and the like, showed superior storage stability even under high temperature high humidity (without packaging) conditions. From these results and the results of the aforementioned Example 1, the production method of the present invention can afford an orally disintegrating tablet which prevents tableting troubles and has superior storage stability.

Experimental Example 2

To examine the storage stability of the orally disintegrating tablet of Example 1, the orally disintegrating tablets of Example 1 and Comparative Example 1 were respectively stored without any packages under conditions of 25° C., 75% RH and 40° C., 75% RH each for one month, and the tablet thickness was measured. The results are shown in Table 2.

TABLE 2

|  | Example 1 | Comparative Example 1 |
|---|---|---|
| At time of start of test | 3.00 mm | 2.98 mm |
| (without packaging) 25° C., 75% RH, one month | 3.04 mm | 3.05 mm |
| (without packaging) 40° C., 75% RH, one month | 3.05 mm | 3.07 mm |

Table 2 shows that in Example 1, the increase in the tablet thickness after one month storage without any packages under the conditions of 25° C., 75% RH and 40° C., 75% RH was 0.04 mm and 0.05 mm, respectively. On the contrary, it was 0.07 mm and 0.09 mm in Comparative Example 1.

From the above-mentioned results, it was shown that the orally disintegrating tablet of Example 1 shows a small change in tablet thickness even under high temperature and high humidity (without packaging) conditions, and show more superior storage stability. From these results and the results of the aforementioned Example 1, the production method of the present invention can afford an orally disintegrating tablet which prevents tableting troubles and has superior storage stability.

Experimental Example 3

The orally disintegrating tablets produced in Examples 3 and 4 were measured for the tensile strength and friability. The tensile strength was calculated by the following formula from the breaking area force determined by a Schleuniger hardness tester (Dr. Schleuniger Pharmatron AG).

$$\text{tensile strength } (N/cm^2) = 2 \times \text{breaking force } (N)/(\pi \times \text{tablet diameter (cm)} \times \text{tablet thickness (cm)})$$

The friability was measured by 25 rpm/min×20 min=500 rpm.

The results are shown in Table 3.

TABLE 3

|  | tensile strength ($N/cm^2$) | friability (%) | hardness (kg) |
|---|---|---|---|
| Example 3 | 167 | 1.23 | about 4.5 |
| Example 4 | 209 | 1.08 | about 5.5 |

From the above-mentioned results, the addition of thaumatin, the preparation of Example 4 increased tensile strength, decreased friability and improved moldability as compared to the preparation of Example 3 free of thaumatin.

As mentioned above, by the addition of thaumatin, the orally disintegrating tablet of Example 4 showed improved moldability and increased hardness at a similar tableting pressure as compared to Example 3.

Experimental Example 4

To examine the storage stability of the orally disintegrating tablets of Examples 8 and 9, the orally disintegrating tablets of Examples 8 and 9 were respectively stored without any packages under conditions of 25° C., 75% RH and 40° C., 75% RH each for one month, and the hardness (kg) was measured. The results are shown in Table 4.

TABLE 4

| storage conditions | Example 8 | Example 9 |
|---|---|---|
| At time of start of test | 4.0 kg | 3.5 kg |
| (without packaging) 25° C., 75% RH, one month | 3.5 kg | 4.0 kg |
| (without packaging) 40° C., 75% RH, one month | 3.7 kg | 3.5 kg |

From the above-mentioned results, the orally disintegrating tablet according to the formulation and production method of the present invention had superior storage stability even under high temperature and high humidity (without packaging) conditions, irrespective of the presence or absence of powder hydrogenated maltose starch syrup.

INDUSTRIAL APPLICABILITY

The orally disintegrating tablet of the present invention can be easily produced by simple steps, is rapidly disintegrated in an oral cavity, has desired appropriated hardness, and is superior in storage stability.

Using the production method of the present invention, an orally disintegrating tablet, which is rapidly disintegrated in an oral cavity, has desired appropriate hardness, and is superior in the storage stability, can be easily produced by simple steps.

This application is based on Japanese patent application No. 2007-340704, the contents of which are incorporated in full herein.

The invention claimed is:

1. An orally disintegrating tablet comprising
    (a) one or more saccharides or sugar alcohols selected from mannitol, lactose, xylitol, sucrose, erythritol and glucose,
    (b) low substituted hydroxypropylcellulose, and
    (c) 0.1-0.35 wt % powder hydrogenated maltose starch syrup,
    wherein
    the tablet is produced by steps of granulating a composition comprising components (a), (b), and (c) by an agitation granulation method, and compression-molding the obtained granulation product, and
    the tablet is substantially free of a starch disintegrant.

2. The orally disintegrating tablet according to claim 1, wherein the saccharide or sugar alcohol of component (a) has an average particle size of not more than 50 μm.

3. The orally disintegrating tablet according to claim 1, wherein the saccharide or sugar alcohol of component (a) is mannitol or lactose.

4. A method of producing an orally disintegrating tablet substantially free of a starch disintegrant, comprising steps of granulating a composition comprising
    (a) one or more saccharides or sugar alcohols selected from mannitol, lactose, xylitol, sucrose, erythritol and glucose,
    (b) low substituted hydroxypropylcellulose, and
    (c) 0.1-0.35 wt % powder hydrogenated maltose starch syrup,
    by an agitation granulation method, and compression-molding the obtained granulation product.

5. The production method according to claim 4, wherein the saccharide or sugar alcohol of component (a) has an average particle size of not more than 50 μm.

6. The production method according to claim 4, wherein the saccharide or sugar alcohol of component (a) is mannitol or lactose.

* * * * *